US010327925B2

(12) United States Patent
Boyle

(10) Patent No.: US 10,327,925 B2
(45) Date of Patent: Jun. 25, 2019

(54) ENDOLUMINAL DEVICE FOR IN VIVO DELIVERY OF BIOACTIVE AGENTS

(71) Applicant: Vactronix Scientific, LLC, Fremont, CA (US)

(72) Inventor: Christopher T. Boyle, Flushing, NY (US)

(73) Assignee: Vactronix Scientific, LLC, Fremont, CA (US)

( * ) Notice: Subject to any disclaimer, the term of this patent is extended or adjusted under 35 U.S.C. 154(b) by 0 days.

(21) Appl. No.: 14/249,278

(22) Filed: Apr. 9, 2014

(65) Prior Publication Data

US 2014/0303716 A1 Oct. 9, 2014

Related U.S. Application Data

(63) Continuation of application No. 13/412,407, filed on Mar. 5, 2012, now Pat. No. 8,697,175, which is a continuation of application No. 12/837,443, filed on Jul. 15, 2010, now Pat. No. 8,128,690, which is a
(Continued)

(51) Int. Cl.
| | |
|---|---|
| *A61F 2/91* | (2013.01) |
| *A61F 2/915* | (2013.01) |
| *A61L 31/16* | (2006.01) |
| *A61M 31/00* | (2006.01) |

(52) U.S. Cl.
CPC .............. *A61F 2/91* (2013.01); *A61F 2/915* (2013.01); *A61L 31/16* (2013.01); *A61M 31/00* (2013.01); *A61F 2002/91541* (2013.01); *A61F 2230/001* (2013.01); *A61F 2250/0067* (2013.01); *A61F 2250/0068* (2013.01)

(58) Field of Classification Search
CPC ........................................................ A61F 2/06
USPC ............................................................ 623/1
See application file for complete search history.

(56) References Cited

U.S. PATENT DOCUMENTS

| 3,797,485 A | 3/1974 | Urquhart ...................... 128/213 |
| 4,203,442 A | 5/1980 | Michaels ...................... 128/260 |
| 4,309,776 A | 1/1982 | Berguer ............................... 3/1 |

(Continued)

FOREIGN PATENT DOCUMENTS

| EP | 0 528 039 | 2/1993 | ............. A61L 27/00 |
| EP | 0 875 218 | 4/1998 | ............... A61L 2/06 |

(Continued)

OTHER PUBLICATIONS

Alt, E., et al., "Antithrombotic stent coatings: hirudin/iloprost combination" *Semin Interv Cardiol.*, 3:3-4; PMID: 10406690 (Sep.-Dec. 1998).

(Continued)

*Primary Examiner* — Andrew J Bowman
(74) *Attorney, Agent, or Firm* — David G. Rosenbaum; Benjamin D. Rotman; Rosenbaum IP, P.C.

(57) ABSTRACT

The present invention consists of an implantable structural element for in vivo delivery of bioactive active agents to a situs in a body. The implantable structural element may be configured as an implantable prosthesis, such as an endoluminal stent, cardiac valve, osteal implant or the like, which serves a dual function of being prosthetic and a carrier for a bioactive agent. Alternatively, the implantable structural element may simply be an implantable article that serves the single function of acting as a time-release carrier for the bioactive agent.

14 Claims, 3 Drawing Sheets

Related U.S. Application Data continuation of application No. 09/716,146, filed on Nov. 17, 2000, now Pat. No. 8,252,044.

(56) References Cited

U.S. PATENT DOCUMENTS

| | | |
|---|---|---|
| 4,464,450 A | 8/1984 | Teuscher .................... 430/59 |
| 4,479,796 A | 10/1984 | Kallok ......................... 604/93 |
| 5,002,661 A | 3/1991 | Chick et al. ................. 210/192 |
| 5,062,829 A | 11/1991 | Pryor et al. .................. 604/57 |
| 5,180,366 A | 1/1993 | Woods ......................... 604/96 |
| 5,201,778 A | 4/1993 | Brotzu et al. ................ 623/66 |
| 5,234,456 A | 8/1993 | Silvestrini ................... 606/194 |
| 5,282,823 A | 2/1994 | Schwartz et al. ............ 606/198 |
| 5,295,962 A | 3/1994 | Crocker et al. .............. 604/101 |
| 5,304,121 A | 4/1994 | Sahatjian ...................... 604/53 |
| 5,306,250 A | 4/1994 | March et al. ................ 604/104 |
| 5,342,348 A | 8/1994 | Kaplan ....................... 604/891.1 |
| 5,370,681 A | 12/1994 | Herweck et al. ............. 623/1 |
| 5,383,927 A | 1/1995 | De Goicoechea et al. ....... 623/1 |
| 5,383,928 A | 1/1995 | Scott et al. .................... 623/1 |
| 5,411,550 A | 5/1995 | Herweck et al. ............. 623/1 |
| 5,421,826 A | 6/1995 | Crocker et al. .............. 604/53 |
| 5,423,885 A | 6/1995 | Williams ........................ 623/1 |
| 5,429,634 A | 7/1995 | Narciso, Jr. ................. 604/890.1 |
| 5,441,551 A | 8/1995 | Khosravi et al. ............. 606/194 |
| 5,443,458 A | 8/1995 | Eury ............................. 604/891.1 |
| 5,443,496 A | 8/1995 | Schwartz et al. ............. 623/1 |
| 5,449,382 A | 9/1995 | Dayton .......................... 623/1 |
| 5,500,013 A | 3/1996 | Buscemi et al. ............... 623/1 |
| 5,575,818 A | 11/1996 | Pinchuk ........................ 623/1 |
| 5,591,224 A | 1/1997 | Schwartz et al. ............. 623/1 |
| 5,599,352 A | 2/1997 | Dinh et al. .................... 623/1 |
| 5,609,629 A | 3/1997 | Fearnot et al. ............... 623/1 |
| 5,632,772 A | 5/1997 | Alcime et al. ................. 623/1 |
| 5,697,967 A | 12/1997 | Dinh et al. .................... 623/1 |
| 5,843,172 A | 12/1998 | Yan ............................... 623/1 |
| 5,873,904 A | 2/1999 | Ragheb et al. ................ 623/1 |
| 5,902,266 A | 5/1999 | Leone et al. .................. 604/53 |
| 5,925,074 A | 7/1999 | Gingras et al. ............... 623/1 |
| 5,972,027 A | 10/1999 | Johnson ........................ 623/1 |
| 6,008,980 A * | 12/1999 | Stevenson et al. ........... 361/302 |
| 6,019,784 A * | 2/2000 | Hines ............................ 128/898 |
| 6,063,101 A | 3/2000 | Jacobsen et al. ............. 606/194 |
| 6,071,305 A | 6/2000 | Brown et al. ................. 623/1 |
| 6,096,070 A | 8/2000 | Ragheb et al. ................ 623/1 |
| 6,099,561 A | 8/2000 | Alt ............................... 623/1.44 |
| 6,099,562 A | 8/2000 | Ding et al. ................... 623/1.46 |
| 6,099,563 A | 8/2000 | Zhong .......................... 623/1.46 |
| 6,120,536 A | 9/2000 | Ding et al. ................... 623/1.43 |
| 6,187,370 B1 | 2/2001 | Dinh et al. ................... 427/2.24 |
| 6,202,304 B1 | 3/2001 | Shatz ............................ 29/896.6 |
| 6,248,401 B1 | 6/2001 | Chiang et al. ............... 427/255.7 |
| 6,258,121 B1 | 7/2001 | Yang et al. ................... 623/1.46 |
| 6,267,782 B1 | 7/2001 | Ogle et al. .................... 623/1.1 |
| 6,274,014 B1 | 8/2001 | Matsumoto et al. ....... 204/298.11 |
| 6,284,305 B1 | 9/2001 | Ding et al. ................... 427/2.28 |
| 6,287,430 B1 | 9/2001 | Matsumoto et al. ....... 204/192.12 |
| 6,287,628 B1 | 9/2001 | Hossainy et al. ............. 427/2.3 |
| 6,299,604 B1 | 10/2001 | Ragheb et al. ................ 604/265 |
| 6,379,381 B1 | 4/2002 | Hossainy et al. ............. 623/1.42 |
| 6,379,382 B1 | 4/2002 | Yang ............................. 623/1.42 |
| 6,471,721 B1 | 10/2002 | Dang ............................ 623/1.34 |
| 6,491,666 B1 | 12/2002 | Santini, Jr. et al. .......... 604/191 |
| 6,491,720 B1 | 12/2002 | Vallana et al. ................ 623/1.42 |
| 6,530,951 B1 | 3/2003 | Bates et al. .................. 623/1.45 |
| 6,652,582 B1 | 11/2003 | Stinson ......................... 623/1.39 |
| 6,709,379 B1 | 3/2004 | Brandau et al. ............... 600/3 |
| 6,719,805 B1 | 4/2004 | Ahern ......................... 623/23.74 |
| 6,758,859 B1 | 7/2004 | Dang et al. ................... 623/1.15 |
| 7,235,096 B1 | 6/2007 | Van Tassel et al. .......... 623/1.15 |
| 2001/0000802 A1 | 5/2001 | Soykan et al. ................ 623/1.13 |
| 2001/0003146 A1 | 6/2001 | Jalisi et al. ................... 600/585 |
| 2001/0014813 A1 * | 8/2001 | Saadat et al. ................ 606/198 |
| 2001/0016726 A1 | 8/2001 | Dubrul et al. ................ 604/509 |
| 2001/0021415 A1 | 9/2001 | Kido et al. ................... 427/255.23 |
| 2001/0037144 A1 | 11/2001 | Kim et al. .................... 623/1.15 |
| 2002/0007209 A1 | 1/2002 | Scheeder et al. ............. 623/1.15 |
| 2002/0193336 A1 | 12/2002 | Elkins et al. ................. 514/44 |
| 2003/0105512 A1 | 6/2003 | Kanesaka ..................... 623/1.15 |
| 2004/0143322 A1 | 7/2004 | Litvack et al. ............... 623/1.42 |
| 2011/0091515 A1 | 4/2011 | Zilberman et al. ........... 424/409 |

FOREIGN PATENT DOCUMENTS

| | | | |
|---|---|---|---|
| JP | 09-099056 | 4/1997 | ............. A61L 31/00 |
| WO | WO 1994/18906 | 9/1994 | ............. A61L 2/02 |
| WO | WO 1997/46268 | 12/1997 | ............. A61L 29/00 |
| WO | WO 1998/058600 | 12/1998 | ............. A61F 2/06 |
| WO | WO 1999/023977 | 5/1999 | ............. A61F 2/06 |
| WO | WO 1999/064086 | 12/1999 | ............. A61L 27/00 |
| WO | WO 2000/018327 | 4/2000 | ............. A61F 2/06 |
| WO | WO 2000/025841 | 5/2000 | ............. A61L 31/14 |
| WO | WO 2000/074584 | 12/2000 | ............. A61B 19/00 |
| WO | WO 2001/012158 | 2/2001 | ............. A61K 9/02 |
| WO | WO 2001/017577 | 3/2001 | ............. A61L 31/14 |
| WO | WO 2001/035865 | 5/2001 | ............. A61F 2/06 |
| WO | WO 2001/055473 | 8/2001 | ............. C23C 14/00 |
| WO | WO 2001/066036 | 9/2001 | ............. A61F 2/06 |
| WO | WO 2001/066161 | 9/2001 | ............. A61L 27/16 |
| WO | 2001/087409 | 11/2001 | |

OTHER PUBLICATIONS

Edelman, et al., "Hoop dreams", *Circulation*, 94: 10 pages (1996).

Ferns, Gordon, A.A., et al., "The mechanisms of coronary restenosis: Insights from experimental models", *International Journal of Experimental Pathology*, 81: 63-88 (2000).

Gershlick, "Local delivery of glycoprotein lib/IIIa receptor inhibits using drug eluting stents", *Dept of Cardiology*, PMID: 10406691 (Sep.-Dec. 1998).

Herdeg, et al., "Antiproliferative stent coatings: Taxol and related compounds", *Semin Interv Cardiol, Dept. of Medicine*, University of Tubingen, Germany, 3:3: PMID: 10406693 (Sep.-Dec. 1998).

Herrman, et al., "Antithrombogenic coating of stents using a biodegradable drug delivery technology", *Thromb Haemost*, 82: 51-57 (1999).

Hunter, et al., "Local delivery of chemotherapy: A supplement to existing cancer treatments, a case of surgical pastes and coated stents", *Advanced Drug Delivery Reviews*, 26: 199-207 (1997)

Kruse, et al., "Basic investigations, local drug delivery of argatroban from a polymeric-metallic composite stent reduces platelet deposition in a swine coronary model", *Catherization and Cardiovascular Interventions*, 46: 503-507 (1999).

Mitchel, et al., "Enhanced intracoronary thrombolysis with urokinase using a novel, local drug delivery system" *Circulation*, 91: 17 pages (1995).

Raman, et al., "Coated stents: Local pharmacology", *Semin Interv Cardiol, Brigham and Women's Hospital*, Harvard Medical School, Boston, MA, 3:304: PMID 10406682 (Sep.-Dec. 1998).

Robinson, et al., "Pharmacokinetics and tissue localization of antisense oligonucleotides in balloon-injured pig coronary arteries after local delivery with iontophoretic balloon catheter", *Catherization and Cardiovascular Diagnosis*, 41: 354-359 (1997)

Van Moorleghem, et al., "Shape memory and superelastic alloys: The new medical materials with growing demand", *Bio-Medical Materials and Engineering*, 8: 56-60 (1998).

Whelan, et al., "Mechanisms of drug loading and release kinetics", *Semin Interv Cardiol, Dept. of Cardiology, Thoraxcenter*, Erasmus University Rotterdam, The Netherlands, 3:3-4: PMID: 10406681 (Sep.-Dec. 1998).

Ye, et al., "Bioresorbable microporous stents deliver recombinant adenovirus gene transfer vectors to the arterial wall", *Annals of Biomedical Engineering* 26: 398-408 (1998).

Yla-Herttuala, Seppo, "Cariovascular gene therapy (statistical data included)", *Lancet*, 23 pages (Jan. 15, 2000).

\* cited by examiner

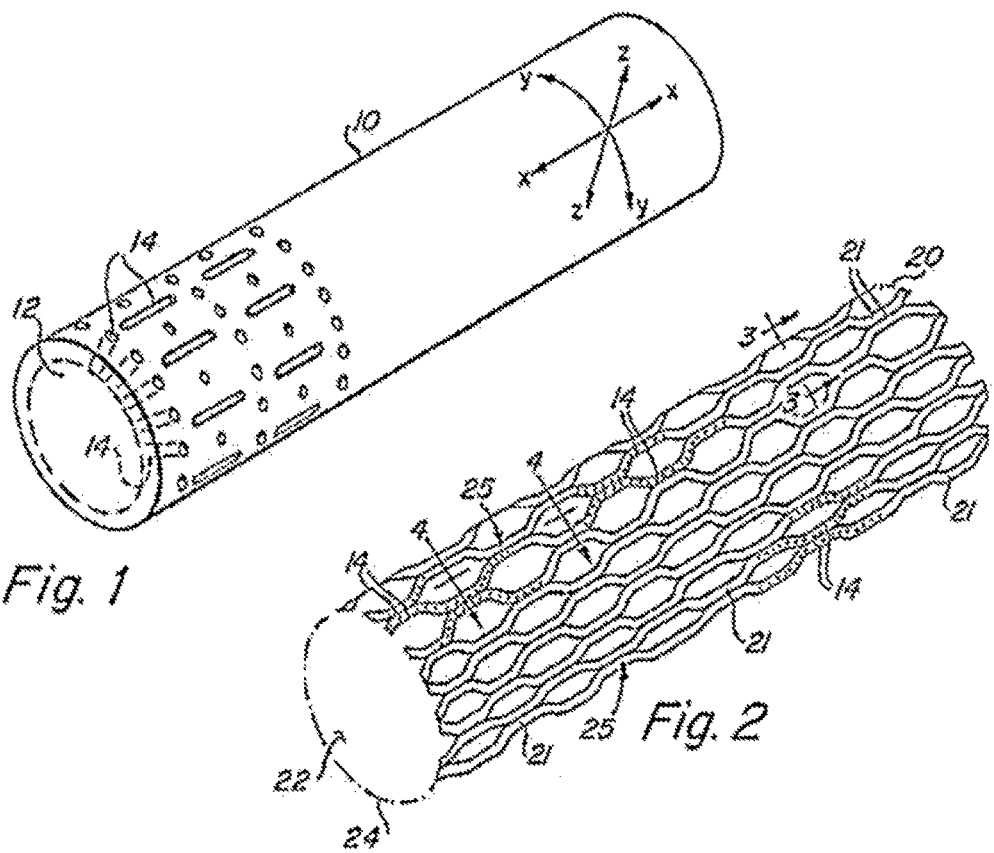
Fig. 1
Fig. 2
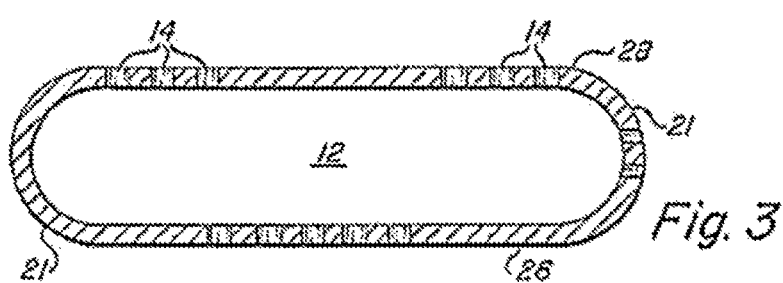
Fig. 3
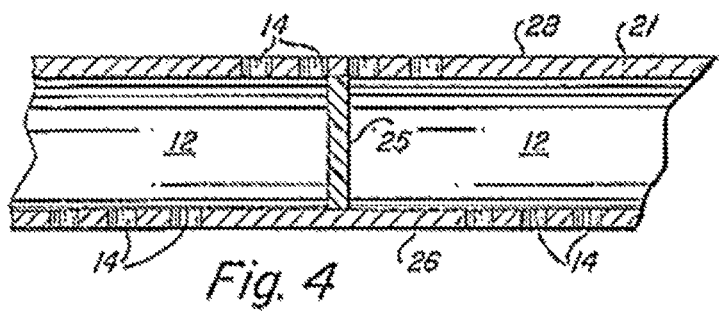
Fig. 4

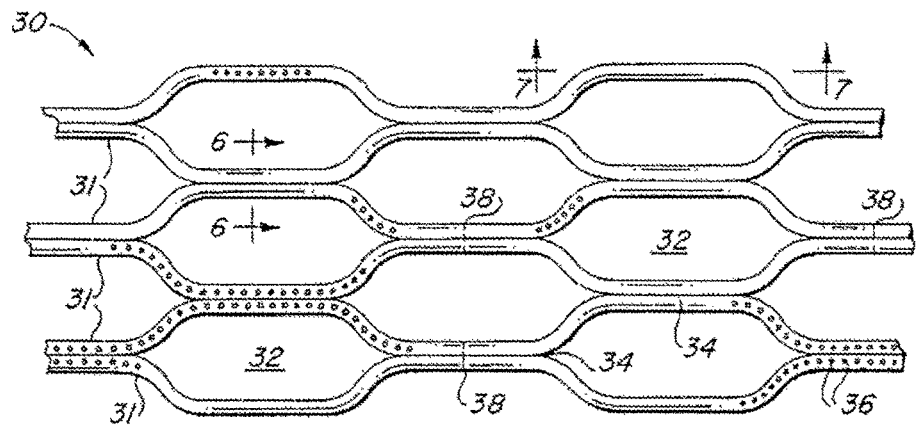
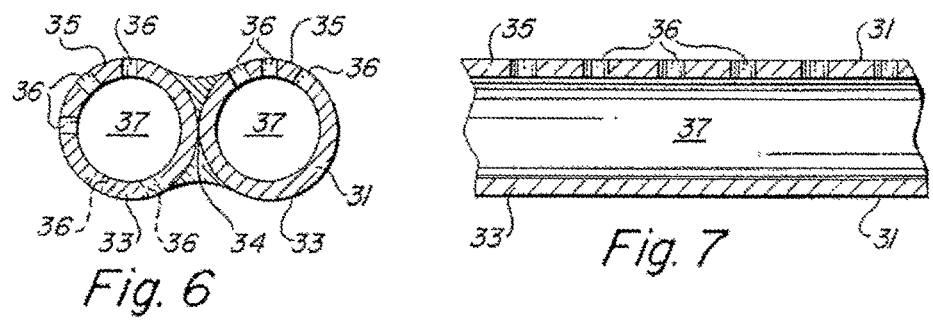
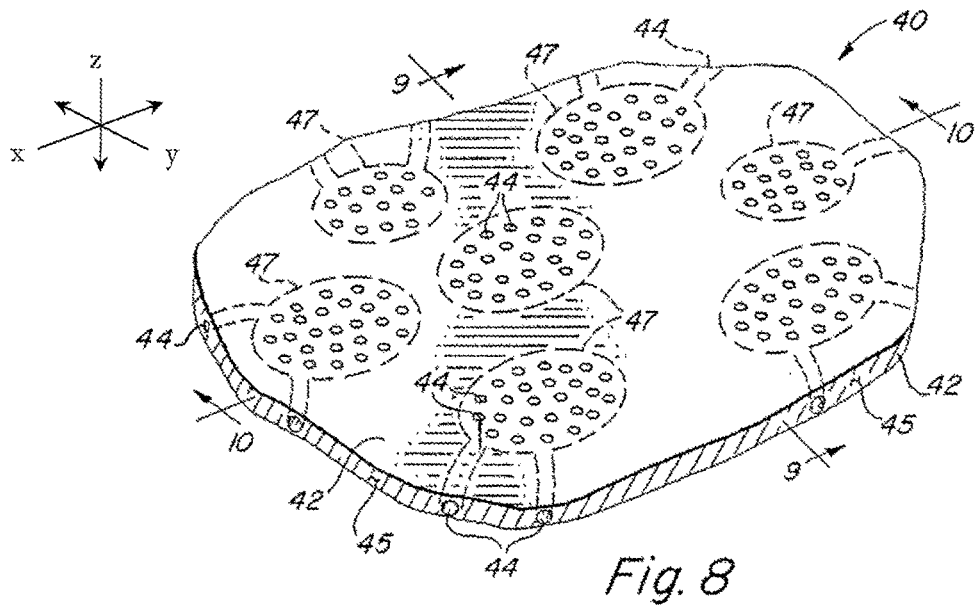

ENDOLUMINAL DEVICE FOR IN VIVO DELIVERY OF BIOACTIVE AGENTS

CROSS REFERENCE TO RELATED APPLICATIONS

This application is a continuation of U.S. patent application Ser. No. 13/412,407, filed Mar. 5, 2012, now U.S. Pat. No. 8,697,175, which is a continuation of U.S. patent application Ser. No. 12/837,443, filed Jul. 15, 2010, now U.S. Pat. No. 8,128,690, and U.S. patent application Ser. No. 09/716,146, filed Nov. 17, 2000, now U.S. Pat. No. 8,252,044, all herein incorporated by reference by their entireties.

BACKGROUND OF THE INVENTION

The present invention relates generally to an implantable device for in vivo delivery of bioactive compounds. The present invention provides an implantable structural material having a three-dimensional conformation suitable for loading a bioactive agent into the structural material, implanting the structural material in vivo and releasing the bioactive agent from the structural agent to deliver a pharmacologically acceptable level of the bioactive agent to an internal region of a body. More particularly, the present invention relates to an implantable medical device, such as an endoluminal stent, stent-graft, graft, valves, filters, occluders, osteal implant or the like, having cavitated regions with micropores that communicate a bioactive agent from the cavity to an area external the stent.

The present invention may be used for any indication where it is desirable to delivery a bioactive agent to a local situs within a body over a period of time. For example, the present invention may be used in treating vascular occlusive disease, disorders or vascular injury, as an implantable contraceptive for delivery of a contraceptive agent delivered intrauterine or subcutaneously, to carry an anti-neoplastic agent or radioactive agent and implanted within or adjacent to a tumor, such as to treat prostate cancer, for time-mediated delivery of immunosuppresents, antiviral or antibiotic agents for treating of autoimmune disorders such as transplantation rejection or acquired immune disorders such as HIV, or to treat implant or non-implant-related inflammation or infections such as endocarditis.

Occlusive diseases, disorders or trauma cause patent body lumens to narrow and restrict the flow or passage of fluid or materials through the body lumen. One example of occlusive disease is arteriosclerosis in which portions of blood vessels become occluded by the gradual build-up of arteriosclerotic plaque, this process is also known as stenosis. When vascular stenosis results in the functional occlusion of a blood vessel the vessel must be returned to its patent condition. Conventional therapies for treatment of occluded body lumens include dilatation of the body lumen using bioactive agents, such as tissue plasminogen activator (TPA) or vascular endothelial growth factor (VEGF) and fibroblast growth factor (FGF) gene transfers which have improved blood flow and collateral development in ischemic limb and myocardium (S. Yla-Herttuala, *Cardiovascular gene therapy*, Lancet, Jan. 15, 2000), surgical intervention to remove the blockage, replacement of the blocked segment with a new segment of endogenous or exogenous graft tissue, or the use of a catheter-mounted device such as a balloon catheter to dilate the body lumen or an artherectomy catheter to remove occlusive material. The dilation of a blood vessel with a balloon catheter is called percutaneous transluminal angioplasty. During angioplasty, a balloon catheter in a deflated state is inserted within an occluded segment of a blood vessel and is inflated and deflated a number of times to expand the vessel. Due to the inflation of the balloon catheter, the plaque formed on the vessel walls cracks and the vessel expands to allow increased blood flow through the vessel.

In approximately sixty percent of angioplasty cases, the blood vessel remains patent. However, the restenosis rate of approximately forty percent is unacceptably high. Endoluminal stents of a wide variety of materials, properties and configurations have been used post-angioplasty in order to prevent restenosis and loss of patency in the vessel.

While the use of endoluminal stents has successfully decreased the rate of restenosis in angioplasty patients, it has been found that a significant restenosis rate continues to exist even with the use of endoluminal stents. It is generally believed that the post-stenting restenosis rate is due, in major part, to a failure of the endothelial layer to regrow over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, Nitinol, etc. customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is considered critical for maintaining vasculature patency and preventing low-flow thrombosis. To prevent restenosis and thrombosis in the area where angioplasty has been performed, anti-thrombosis agents and other biologically active agents can be employed.

It has been found desirable to deliver bioactive agents to the area where a stent is placed concurrently with stent implantation. Many stents have been designed to deliver bioactive agents to the anatomical region of stent implantation. Some of these stents are biodegradable stents which are impregnated with bioactive agents. Examples of biodegradable impregnated stents are those found in U.S. Pat. Nos. 5,500,013, 5,429,634, and 5,443,458. Other known bioactive agent delivery stents include a stent disclosed in U.S. Pat. No. 5,342,348 in which a bioactive agent is impregnated into filaments which are woven into or laminated onto a stent. U.S. Pat. No. 5,234,456 discloses a hydrophilic stent which can include a biologically active agent disposed within the hydrophilic material of the stent. Other bioactive agent delivery stents disclosed in U.S. Pat. Nos. 5,201,778, 5,282,823, 5,383,927; 5,383,928, 5,423,885, 5,441,515, 5,443,496, 5,449,382, 4,464,450, and European Patent Application No. 0 528 039. Other devices for endoluminal delivery of bioactive agents are disclosed in U.S. Pat. Nos. 3,797,485, 4,203,442, 4,309,776, 4,479,796, 5,002,661, 5,062,829, 5,180,366, 5,295,962, 5,304,121, 5,421,826, and International Application No. WO 94/18906. A directional release bioactive agent stent is disclosed in U.S. Pat. No. 6,071,305 in which a stent is formed of a helical member that has a groove in the abluminal surface of the helical member. A bioactive agent is loaded into the groove prior to endoluminal delivery and the bioactive agent is therefore in direct apposition to the tissue that the bioactive agent treats. Finally, International Application No. WO 00/18327 discloses a drug delivery stent in which a tubular conduit is wound into a helical stent. The tubular conduit has either a single continuous lumen or dual continuous lumens that extend the entire length of the conduit. The tubular conduit has regions or segments thereof that have pores to permit drug "seepage" from the conduit. One end of the tubular conduit is in fluid flow communication with a fluid delivery catheter, which introduces a fluid, such as a drug into the continuous lumen and through the pores.

Where biodegradable or non-biodegradable polymer-based or polymer-coated stents have been used, the polymers cause an immune inflammatory response once the drug is eluted out of the polymer. Where a polymer is employed as the bioactive agent carrier, it is, therefore, desirable to isolate the polymer from body tissues in order to limit the immune inflammatory response after the bioactive agent has eluted as can be accomplished with the present invention.

SUMMARY OF THE INVENTION

As used herein the term "bioactive agent" is intended to include one or more pharmacologically active compounds which may be in combination with pharmaceutically acceptable carriers and, optionally, additional ingredients such as antioxidants, stabilizing agents, permeation enhancers, and the like. Examples of bioactive agents which may be used in the present invention include but are not limited to antiviral drugs, antibiotic drugs, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, immunosuppresents, such as rapomycin, beta and calcium channel blockers, genetic materials including DNA and RNA fragments, complete expression genes, antibodies, lymphokines, growth factors (vascular endothelial growth factor (VEGF) and fibroblast growth factor (FGF)), prostaglandins, leukotrienes, laminin, elastin, collagen, nitric oxide (NO) and integrins.

The inventive structural material has a three dimensional conformation having a geometry and construction in which there is an internal cavity or a plurality of internal cavities within the structural material and a conduit or opening or plurality of conduits or openings which communicate between the internal cavity and external the structural material. The three dimensional conformation of the structural material may assume a cylindrical, tubular, planar, spherical, curvilinear or other general shape which is desired and suited for a particular implant application. For example, in accordance with the present invention there is provided an endoluminal stent that is made of a plurality of structural members that define a generally tubular shape for the endoluminal stent. At least some of the plurality of structural members are comprised of the inventive structural material and have at least one internal cavity and at least one conduit or opening which communicates between the internal cavity and external the stent. Alternate types of implantable devices contemplated by the present invention include, without limitation, stent-grafts, grafts, heart valves, venous valves, filters, occlusion devices, catheters, osteal implants, implantable contraceptives, implantable anti-tumor pellets or rods, or other implantable medical devices.

The inventive stent for delivery of bioactive agents consists generally of a plurality of structural elements, at least some of which have internal cavities that retain the bioactive agents, and openings that pass between the internal cavities and the surface of the structural elements to communicate the bioactive agent from the internal cavity to external the stent. Other than described herein, the present invention does not depend upon the particular geometry, material, material properties or configuration of the stent.

Because of their use as a structural scaffold and the requirement that stents be delivered using transcatheter approaches, stents necessarily are delivered in a reduced diametric state and are expanded or allowed to expand in vivo to an enlarged diametric state. Thus, all stents have certain structural regions that are subject to higher stress and strain conditions than other structural regions of the stent. Thus, it may be advantageous to position the internal cavities that retain the bioactive agents in structural regions of the stent that are subjected to relatively lower stress and strain during endoluminal delivery and deployment. Alternatively, where delivery of a bolus of a bioactive agent is desired, internal cavities may be positioned in regions that undergo large deformation during delivery and deployment thereby forcing the bioactive agent out of the internal cavity under the positive pressure exerted by the deformation. Diffusion forces, then, elute remaining bioactive agent present in either the region of large deformation or the regions of lower stress and strain.

BRIEF DESCRIPTION OF THE DRAWINGS

FIG. 1 is a perspective view of an implantable member in accordance with the present invention.

FIG. 2 is a perspective view of an endoluminal stent having a plurality of structural member in accordance with the present invention.

FIG. 3 is a cross-sectional view taken along line 3-3 of FIG. 2.

FIG. 4 is a cross-sectional view taken along line 4-4 of FIG. 2.

FIG. 5 is a fragmentary perspective view of an alternative embodiment of the inventive endoluminal stent in accordance with the present invention.

FIG. 6 is a cross-sectional view taken along line 6-6 of FIG. 5.

FIG. 7 is a cross-sectional view taken along line 7-7 of FIG. 5.

FIG. 8 is a perspective view of a planar structural element for delivery of a bioactive agent in accordance with the present invention.

DETAILED DESCRIPTION OF THE PREFERRED EMBODIMENTS

Figure 9:
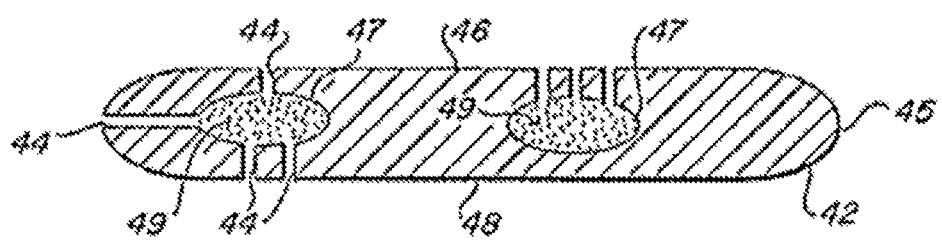
FIG. 9 is a cross-sectional view taken along line 9-9 of FIG. 8.

As noted above, the term "bioactive agent" is intended to encompass one or more pharmacologically active compounds which may be in combination with pharmaceutically acceptable carriers and, optionally, additional ingredients such as antioxidants, stabilizing agents, permeation enhancers, and the like. Examples of bioactive agents which may be used in the present invention include but are not limited to antibiotic drugs, antiviral drugs, neoplastic agents, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, immunosuppresents, such as rapomycin, beta and calcium channel blockers, genetic materials including DNA and RNA fragments, complete expression genes, antibodies, lymphokines, growth factors (vascular endothelial growth factor (VEGF) and fibroblast growth factor (FGF)), prostaglandins, leukotrienes, laminin, elastin, collagen, nitric oxide (NO), and integrins.

With particular reference to FIG. 1, the present invention consists generally of a body element 10 having a three-dimensional conformation defining X, Y and Z-axes of the body element 10 and at least one of a plurality of interior cavities 12 defined within the body element 10, and at least one of a plurality of passages or pores 14 which communicate between the at least one of a plurality of interior cavities 12 and exterior to the body element 10. While the body element 10 depicted in FIG. 1 is of a generally cylindrical three dimensional conformation, alternative three dimensional conformations, such as planar, spherical, ovular, tetrahedral, curvilinear or virtually any other three dimensional conformation suitable for implantation into a living body are contemplated by the present invention. The plurality of passages 14 have dimensions sufficient to permit the bioactive agent to elute by diffusion, osmotic pressure or under the influence of a positive pressure applied by cellular in-growth into the plurality of interior cavities 12.

The location of the plurality of passages 14 is dependent upon the particular application for which the body element 10 is intended. For example, with particular reference to FIGS. 2-4, where the body element 10 is a tubular body 20 made of a plurality of interconnected structural elements 21, such as a stent, stent-graft or graft, which defines a central lumen 22 and has openings 24 at opposing proximal and distal ends of the tubular body 20, the plurality of passages 14 are formed in at least some of the plurality of interconnected structural elements 21 and may be disposed on only the luminal surface 26 or only on the abluminal surface 28 of the tubular body 20, or both. Pores 14 on the luminal surface 26 only will communicate the bioactive agent into the lumen 22 and any body fluid, such as blood, flowing through the central lumen 22 of the tubular body 20, while pores 14 on only the abluminal surface 28 will communicate the bioactive agent to the abluminal surface 28 of the tubular body 20. At least a portion of some of the plurality of interior cavities 12 may communicate with either the proximal or distal ends of at least some of the plurality of interconnected structural elements 21. In this case, the proximal and/or distal ends of at least some of the plurality of interconnected structural elements 21 may be tapered such as to be self-cannulating into body tissue during delivery and deployment. The bioactive agent retained within the internal cavity 12 which communicates with the proximal and/or distal ends of at least some of the plurality of interconnected structural elements 21 will then pass out of the proximal and/or distal ends in much the same manner as fluid flowing through an injection needle.

In addition to the foregoing positioning of the pores 14, both the plurality of internal cavities 12 and the plurality of pores 14 may be positioned to be discontinuous and in different circumferential or different longitudinal regions of the tubular body 20. Within a single one of the plurality of interconnected structural elements 21, the internal cavities 12 may be separated by a separation member 25, which completely subtends the internal cavity 12, dividing it into discrete discontinuous internal cavities 12. The advantage of forming a plurality of discontinuous internal cavities 12 is that it permits loading of different bioactive agents into different regions of the body member 10 or tubular member 20 to isolate different regions for delivery of different bioactive agents to different sites within a body. For example, a first grouping of a plurality of internal cavities 12 and associated plurality of pores 14 may be located at a proximal end of the tubular body 20, and a second grouping of a plurality of internal cavities 12 and associated plurality of pores 14 may be located at an intermediate region of the tubular body 20, and a third grouping of a plurality of internal cavities 12 and associated plurality of pores 14 may be located at a distal end of the tubular body 20. A first bioactive agent may be loaded into the first and third groupings of a plurality of internal cavities 12, while a second bioactive agent may be loaded into the second grouping of a plurality of internal cavities 12. Where, for example, the tubular body 20 is an endoluminal stent, stent-graft or graft which is implanted post-angioplasty, the proximal and distal ends of the tubular body 20 are anchored adjacent to healthy tissue while the intermediate region of the tubular body 20 is positioned adjacent to the diseased or injured tissue. In this configuration, a first bioactive agent, such as an endothelial growth factor and/or contrast medium to impart enhanced radiopacity to the tubular body 20 may be carried in the first and third groups of a plurality of internal cavities 12 and associated pores 14, while an anticoagulant, such as heparin, may be carried in the second grouping of a plurality of internal cavities 12 and associated pores 14. In this manner, the tubular body has enhanced radiopacity to aid in delivery and deployment and endothelial growth factors to enhance endothelialization of the tubular body 20, while delivering an anticoagulant directly to the site of the tissue lesion.

Moreover, where the internal cavities 12 are discontinuous, the plurality of pores 14 may be configured to include degradable plugs which degrade at different rates to expose different bioactive agents in the internal cavities 12 to the body at different points in time. Alternatively or additionally, the degradable plugs may degrade at different rates to expose the same bioactive agent in different internal cavities 12 at different periods of time to effectively elongate the period of time during which the bioactive agent is delivered.

The body element 10 is preferably formed of a metal such as titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, or stainless steel.

Turning to FIGS. 5-7 there is illustrated an alternative embodiment of the inventive endoluminal stent 30 fabricated from a plurality of tubular structural elements 31 formed into a tubular stent and having a desired geometry. Structural elements 21 may also be known as struts in the field of stents. It will be appreciated that the generally hexagonal cell geometric pattern illustrated in FIG. 5 is merely exemplary and a myriad of different geometries of different geometric complexities are contemplated by the invention. Each of the tubular structural elements 31 has a central lumen that forms the internal cavity 37 within each structural element 31. A plurality of separation member 38 may be provided to subdivide the internal cavity 37 into a plurality of discontinuous internal cavities 37. Each of the tubular structural elements 31 has a plurality of openings 36 which communicate between the internal cavity 37 and one or both of a luminal surface 33 or an abluminal surface 35 of each of the plurality of tubular structural elements 31. The tubular structural elements 31 may assume any transverse cross-sectional configuration having a central lumen.

Those of ordinary skill in the stent forming arts will understand that in order to form a tubular endoluminal stent 30 of tubular elements 31, it is necessary to join at least some of the plurality of tubular elements 31. Conventionally, a plurality of spot-welds 34 serve to interconnect sections of individual tubular elements 31 in juxtaposed relationship to one and other. The plurality of spot welds 34 may also be employed to seal the internal cavity 37 at the position of the spot weld, thereby creating a separation member 38 within the internal cavity 37 of each individual tubular element 31 and forming discontinuous internal cavities 37.

As noted above, the plurality of openings 36 are dimensioned to permit the bioactive agent to elute from the at least one of a plurality of internal cavities 37 and through the associated plurality of openings 36 by diffusion, osmotic pressure or under the influence of a positive pressure applied by cellular in-growth into the plurality of internal cavities 37 or under positive pressure applied by stress and/or strain exerted on the plurality of internal cavities 37 due to deformation of the individual tubular structural elements 31. Additionally, the positioning of the plurality of openings 36 relative to the individual tubular structural elements 31 and to the endoluminal stent as a whole may be adapted to deliver varying quantities of or different bioactive agents from different regions of the tubular structural elements 31 or different regions of the endoluminal stent 30. Moreover, proximal and/or distal ends of individual tubular structural elements 31 may be tapered so as to form self-cannulating ends of the individual tubular structural elements 31 which penetrate body tissue and permit the bioactive agent to be communicated from the internal cavity 37 out the proximal or distal end of the tubular structural element 31 in a manner similar to a hypodermic needle.

Figure 10:
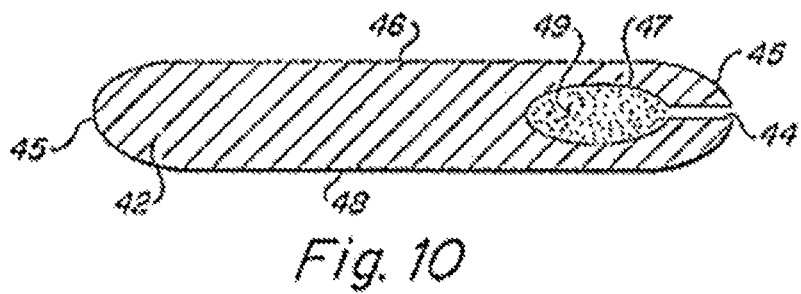
FIG. 10 is a cross-sectional view taken along line 10-10 of FIG. 8.

In accordance with another embodiment of the present invention, and as illustrated in FIGS. 8-10, there is provided an implantable device 40 which consists of a structural body 42 having a three-dimensional conformation extending in the X-axis, Y-axis and Z-axis dimensionally. While the illustrated embodiment of the structural body 42 is planar, those of ordinary skill in the medical device fabrication art will understand that it is within the skill of the artisan to fabricate the structural body 42 of any desired three-dimensional conformation depending upon the desired use and indication of the implantable device 40. The three-dimensional conformation of the structural body 42 may be cylindrical, tubular, quadrilinear, planar, spherical, ovular, tetrahedral, curvilinear or virtually any other three-dimensional conformation suitable for implantation into a living body.

Like the above-described embodiments, the structural body 42 has at least one of a plurality of internal cavities 47, each of which carry a bioactive agent 47, and a plurality of openings 44 which pass from at least one upper 46, lower 48 or lateral 45 surface of the structural body 42, through the Z-axis thickness of the body and communicate with the at least one of a plurality of internal cavities 47 in the structural body 42. Where a plurality of internal cavities 47 are provided within the structural body 42, a plurality of bioactive agents 49 may be loaded into the structural body 42 with one or more bioactive agents 49 being loaded into each of the plurality of internal cavities 47.

Each of the above-described preferred embodiments of the present invention may be fabricated by a number of methods. In accordance with present invention, it is contemplated that either forming wrought metal parts, such as capillary tubing, into the implantable device or forming the implantable devices by vacuum deposition techniques are the preferred method of making the implantable structural elements of the present invention. Where an implantable device is to be fabricated of a plurality of individual tubular elements, such as depicted in FIGS. 5-7, pre-existing microtubular members having an outer diameter, for example, between 60 and 400 μm and a wall thickness of between 10 and 350 μm, may be employed to fabricate extremely small dimensioned devices suitable for intracranial or coronary artery applications. The microtubular members may be formed into a cylindrical endoluminal device, such as by braiding or bending and joining microtubular members together by spot welding. Where ends of the microtubular members are formed to be self-cannulating, the self-cannulating ends may be exposed on the abluminal surface of an endoluminal device at any point along the longitudinal axis thereof. The plurality of openings passing through the wall of each of the individual tubular elements may be formed by microdrilling the openings through the wall and into the internal cavity or lumen of the individual tubular members. The plurality of openings may be laser cut, etched or formed by EDM methods, and may be formed either pre- or post-formation of the tubular elements into the three-dimensional conformation of the implantable device. Where an implantable device is to be formed from non-preexisting structural elements, vacuum deposition techniques may be employed to form the implantable structural body, such as sputtering, reactive ion etching, chemical vapor deposition, plasma vapor deposition, or the like, as are known in the microelectronics fabrication arts and are more fully described in co-pending, commonly assigned U.S. patent application Ser. No. 09/443,929, filed Nov. 19, 1999, which is hereby incorporated by reference. Because, the internal cavities and openings must be formed during deposition, the vacuum deposition techniques must be modified to deposit requisite patterns of sacrificial material to form the regions of the internal cavities and openings, over a base layer of structural material, then depositing a second layer of structural material over the sacrificial material and the base layer. The sacrificial material may then be removed, such as by etching, to leave the internal cavities and plurality of openings formed within the deposited bulk material.

Regardless of which fabrication method is employed, the bioactive agent must be loaded into the internal cavities of the implantable device. Loading of the bioactive agent may be accomplished by flowing a liquid or semi-liquid state of the bioactive agent through the plurality of openings and into the internal cavities, either throughout the entire device or in regions of the implantable device. Flow loading may be facilitated by applying positive pressure, temperature change or both, such as is used in hot isostatic pressing (HIP). In HIP the pressurizing medium is typically a gas, and the process is carried out at elevated temperatures for specific time periods. While HIP is typically utilized to densify materials, to heal casting defects and voids, or to bond similar or dissimilar materials it may be used to drive a fluid or semi-fluid from external the implantable device into the internal cavities of the implantable device. Alternative, diffusion-mediated loading, osmotic loading or vacuum loading may be employed to load the bioactive agent into the internal cavities.

While the present invention has been described with reference to its preferred embodiments, those of ordinary skill in the art will understand and appreciate that variations in structural materials, bioactive agents, fabrication methods, device configuration or device indication and use may be made without departing from the invention, which is limited in scope only by the claims appended hereto.

What is claimed is:

1. A method of making an implantable device comprising:
   a. forming a base layer of structural material;
   b. depositing a pattern of sacrificial material onto the base layer, the sacrificial material forming internal cavity regions;
   c. depositing at least a second layer of structural material over the sacrificial material and over the base layer forming a strut having a an upper surface, lower surface, and lateral surface bounding the sacrificial material;
   d. forming one or more microholes in the structural material providing fluid flow communication between the sacrificial material and the area external to the at least one of upper surface, lower surface, or lateral surface; and
   e. removing the sacrificial material forming at least one internal cavity bound intermediate the upper surface, lower surface, and lateral surface wherein the one or more microholes are in fluid communication with the internal cavity.

2. The method of claim 1, wherein the step of removing the sacrificial material forming at least one internal cavity is performed by etching.

3. The method of claim 1, wherein the strut formed is planar.

4. The method of claim 1, wherein the step of forming one or more holes in the structural material comprises one of the methods of formation selected from the group consisting of microdrilling, laser cutting, etching, and EDM.

5. The method of claim 1, wherein the step of forming a base layer of structural material, comprises using a vacuum deposition technique selected from the group consisting of sputtering, reactive ion etching, chemical vapor deposition, and plasma vapor deposition.

6. The method of claim 1, further comprising the step of depositing a bioactive agent within the internal cavity.

7. The method of claim 6, wherein the step of removing the sacrificial material forming the region of the internal cavity is performed by etching.

8. The method of claim 6, further comprising the step of forming regions of one or more holes with sacrificial material, wherein the step of forming one or more holes in the structural material comprises removing the sacrificial material forming the regions of one or more holes by etching.

9. The method of claim 8, wherein the step of depositing a second layer of structural material over the sacrificial material does not include depositing structural material over the sacrificial material forming regions of one or more holes.

10. The method of claim 6, wherein a plurality of struts are formed resulting in a generally tubular shaped stent structure.

11. An endoluminal stent, comprising:
    a. a plurality of tubular struts, each tubular strut of the plurality of tubular struts having an external surface, an internal surface, a wall thickness intermediate the external and internal surfaces that is substantially uniform about a transverse cross section of the tubular strut, and an internal cavity concentric entirely within the tubular strut along a longitudinal axis of the tubular strut;
    b. a plurality of micropores passing through the wall thickness distributed about the entire circumference of the tubular strut that permit generally omnidirectional fluid flow therethrough from the internal cavity;
    c. a bioactive agent disposed within the internal cavity that elutes from the internal cavity through at least some of the plurality of micropores; and
    d. wherein the plurality of struts are disposed circumferentially forming a tubular stent having a stent central lumen.

12. The endoluminal stent of claim 11, wherein the plurality of tubular struts are operably associated with one another in such a manner as to permit diametric expansion of the endoluminal stent.

13. The endoluminal stent of claim 12, wherein the plurality of tubular struts are in a configuration selected from the group consisting of a grid configuration, a mesh configuration, and a braided configuration.

14. The endoluminal stent of claim 11, wherein the plurality of micropores are dimensioned to permit a bioactive agent to elute from the internal cavity and through the plurality of micro-openings by diffusion, osmotic pressure, under the influence of a positive pressure applied by cellular in-growth into the internal cavity, or under positive pressure applied by stress and/or strain exerted on the at least one cavity due to deformation of the tubular strut.

* * * * *